United States Patent
Indo et al.

(10) Patent No.: US 10,241,030 B2
(45) Date of Patent: Mar. 26, 2019

(54) OPTICAL SPECTROMETER AND DOWNHOLE SPECTROMETRY METHOD

(71) Applicant: Schlumberger Technology Corporation, Sugar Land, TX (US)

(72) Inventors: Kentaro Indo, Sugar Land, TX (US); Kai Hsu, Sugar Land, TX (US); Julian Pop, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/359,345

(22) PCT Filed: Nov. 30, 2012

(86) PCT No.: PCT/US2012/067324
§ 371 (c)(1),
(2) Date: May 20, 2014

(87) PCT Pub. No.: WO2013/082446
PCT Pub. Date: Jun. 6, 2013

(65) Prior Publication Data
US 2014/0293282 A1 Oct. 2, 2014

Related U.S. Application Data

(60) Provisional application No. 61/566,503, filed on Dec. 2, 2011.

(51) Int. Cl.
*G01V 8/12* (2006.01)
*E21B 49/08* (2006.01)
*G01N 21/25* (2006.01)

(52) U.S. Cl.
CPC ............ *G01N 21/255* (2013.01); *E21B 49/08* (2013.01); *E21B 49/088* (2013.01); *G01V 8/12* (2013.01)

(58) Field of Classification Search
CPC ...... E21B 47/102; E21B 49/08; E21B 49/088; G01J 3/42; G01J 3/28; G01N 21/255; G01V 8/12
(Continued)

(56) References Cited

U.S. PATENT DOCUMENTS 5,128,797 A * 7/1992 Sachse ............... G01J 3/08 356/370
5,303,165 A * 4/1994 Ganz et al. ............... 356/319
(Continued)

FOREIGN PATENT DOCUMENTS

KR 10-0360069 B1 11/2002

OTHER PUBLICATIONS

International Search Report for International Application No. PCT/US2012/067324 dated Feb. 18, 2013.

*Primary Examiner* — Dominic J Bologna
(74) *Attorney, Agent, or Firm* — Michael Dae

(57) ABSTRACT

An optical spectrometer includes a near black body light source, a reference detector in a first optical path and a single measurement detector in a second optical path. A sample cell including a fluid flow line may be positioned in the second optical path upstream of the measurement detector. Optical energy may be emitted at a plurality of filament temperatures and first and second sets of optical intensities measured at the reference and measurement detectors. The first and second sets of optical intensities may be processed to compute a substantially continuous transmittance spectrum of a fluid sample in the fluid flow line by inverting the acquired optical intensity measurements.

4 Claims, 4 Drawing Sheets

(58) Field of Classification Search
USPC ....... 356/319–325, 402, 432, 433, 435, 436, 356/440
See application file for complete search history.

(56) References Cited

U.S. PATENT DOCUMENTS

| | | |
|---|---|---|
| 6,768,105 B2 | 7/2004 | Mullins et al. |
| 7,155,076 B2* | 12/2006 | Letant ................. G01N 21/774 385/12 |
| 7,280,214 B2* | 10/2007 | DiFoggio ............. E21B 47/102 356/416 |
| 7,336,356 B2 | 2/2008 | Vannuffelen et al. |
| 7,423,756 B2* | 9/2008 | Gordley ............. G01N 21/3504 250/339.01 |
| 7,511,813 B2 | 3/2009 | Vannuffelen et al. |
| 7,948,620 B2 | 5/2011 | Christian et al. |
| 8,436,296 B2* | 5/2013 | Ford .................... E21B 47/102 250/269.1 |
| 2004/0135106 A1* | 7/2004 | Bolash et al. ............. 250/559.4 |
| 2007/0229834 A1* | 10/2007 | Patel et al. ................... 356/432 |
| 2008/0149819 A1* | 6/2008 | Zhdaneev .................... 250/255 |
| 2010/0027004 A1* | 2/2010 | Bonyuet .................. G01J 3/02 356/326 |
| 2011/0108719 A1* | 5/2011 | Ford ........................ G01J 3/02 250/262 |
| 2011/0108720 A1* | 5/2011 | Ford ...................... E21B 49/08 250/262 |
| 2011/0108721 A1* | 5/2011 | Ford et al. ................. 250/269.1 |

\* cited by examiner

OPTICAL SPECTROMETER AND DOWNHOLE SPECTROMETRY METHOD

FIELD OF THE INVENTION

Disclosed embodiments relate generally to an apparatus and method for acquiring optical spectral data for downhole fluid analysis. More particularly the disclosed embodiments related to an apparatus and method employing a reference detector and a single measurement detector.

BACKGROUND INFORMATION

In order to successfully exploit subterranean hydrocarbon reserves, information about the subsurface formations and formation fluids intercepted by a wellbore is generally required. This information may be obtained via sampling and analyzing formation fluids during various drilling and completion operations. The fluid may be collected and analyzed, for example, to ascertain the petrophysical, mineralogical, and fluid properties of a hydrocarbon containing fluid reservoir. The analysis may be in turn utilized to evaluate the economic viability of the reservoir.

Subterranean reservoirs commonly include a complex mixture of fluids including oil, gas, and water at high temperatures and pressures. In order to evaluate substantially pristine reservoir fluids, recent developments in fluid analysis include techniques for downhole analysis, for example, including downhole (in-situ) optical spectrometry techniques.

Optical spectrometers of the type used in downhole tools are generally based on filter array architecture using optical bandpass filters. Spectrometer input light is distributed on an array of optical bandpass filters and the optical absorption of formation fluids is measured at a fixed number of discrete wavelengths which are limited to the number of filters. Since downhole space constraints provide an upper limit on the number of bandpass filters that may be utilized, spectral resolution tends to be poor. As such, precise spectrum analysis with high wavelength resolution tends not to be possible with a conventional type of downhole spectrometer. It is therefore desirable to improve the operation of downhole spectrometers.

SUMMARY

A disclosed optical spectrometer includes a near black body light source (such as a halogen lamp), a reference detector in a first optical path and a single measurement detector in a second optical path. A sample cell including a fluid flow line may be positioned in the second optical path upstream of the measurement detector. Optical energy may be emitted at a plurality of filament temperatures and first and second sets of optical intensities may be measured at the reference and measurement detectors. The first and second sets of optical intensities may be processed to compute a substantially continuous transmittance spectrum of a fluid sample in the fluid flow line by inverting the acquired optical intensity measurements.

The disclosed embodiments may provide various technical advantages. For example, the disclosed optical spectrometer and spectroscopy method enables a substantially continuous transmittance spectrum of a fluid sample to be recovered. Acquisition of a continuous fluid spectrum may advantageously allow for a full and detailed investigation of the fluid sample.

Moreover, the disclosed optical spectrometer and spectroscopy method makes use of a single measurement detector. The disclosed optical spectrometer may therefore be compact, simple, robust, and cost effective. The use of a single measurement detector also tends to improve reliability and serviceability of the spectrometer.

In one disclosed aspect, a downhole fluid sampling tool includes an inlet port through which formation fluid samples may be drawn and an optical spectrometer. The optical spectrometer includes a near black body light source, a beam splitter optically downstream from the light source and configured to divide incident light into first and second reference and measurement paths, a reference detector deployed in the reference path, a single measurement detector deployed in the measurement path, and a sample cell including a fluid flow in fluid communication with the inlet port, the sample cell being deployed in the measurement path between the beam splitter and the measurement detector.

In another aspect, a disclosed method for obtaining a transmittance spectrum of a fluid sample includes: (a) receiving the fluid sample at an optical spectrometer; (b) emitting near black body optical energy at a plurality of filament temperatures, the optical energy passing through a beam splitter into first and second optical paths, the second optical path passing through the fluid sample; (c) measuring a first set of optical intensities at a reference detector in the first path, the optical intensities in the first set corresponding to the plurality of filament temperatures; (d) measuring a second set of optical intensities at a single measurement detector in the second optical path, the optical intensities in the second set corresponding to the plurality of filament temperatures; and (e) processing the optical intensities measured in (c) and (d) to compute the transmittance spectrum of the fluid sample.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

For a more complete understanding of the disclosed subject matter, and advantages thereof, reference is now made to the following descriptions taken in conjunction with the accompanying drawings, in which.

DETAILED DESCRIPTION

Figure 1:
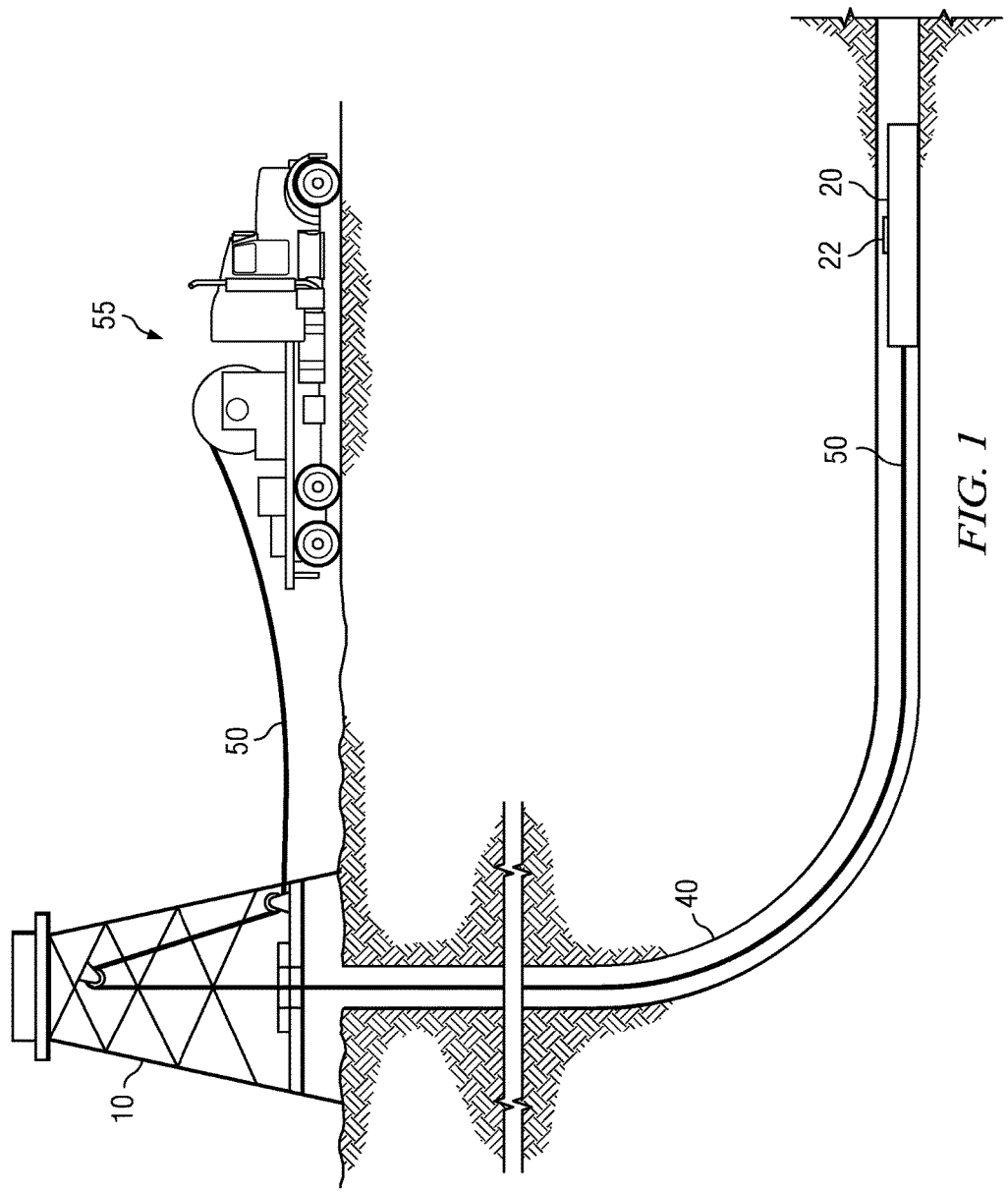
FIG. 1 depicts one example of a rig on which disclosed tool embodiments may be utilized.

FIG. 1 depicts a drilling rig 10 suitable for employing certain downhole tool embodiments disclosed herein. In the depiction, a rig 10 is positioned over (or in the vicinity of) a subterranean oil or gas formation (not shown). The rig may include, for example, a derrick and a hoisting apparatus for lowering and raising various components into and out of the wellbore 40. A downhole wireline sampling tool 20 is deployed in the wellbore 40. The sampling tool may be connected to the surface, for example, via a wireline cable 50 which is in turn coupled to a wireline truck 55.

During a wireline operation, sampling tool 20 may be lowered into the wellbore 40. In a highly deviated borehole, the sampling tool 20 may alternatively or additionally be driven or drawn into the borehole using, for example, a downhole tractor or other conveyance means. The disclosed embodiments are not limited in this regard. Sampling tool 20 may also be conveyed into the borehole 40 using coiled tubing or drill pipe conveyance methodologies.

The example wireline sampling tool 20 described herein may be used to acquire optical spectral data for downhole fluid analysis. Formation fluid samples may be drawn into the sampling tool 20, for example, through an inlet port or probe 22 and passed through a sample cell where the optical spectral data may be acquired. The sampling tool 20 may further include a number of sample bottles (not shown) for obtaining formation fluid samples. While FIG. 1 depicts a wireline sampling tool 20, it will be understood that the disclosed embodiments are not so limited. For example, sampling tool 20 may include a drilling tool such as a measurement while drilling or logging while drilling tool configured for deployment on a drill string. The disclosed embodiments are not limited in these regards.

Figure 2:
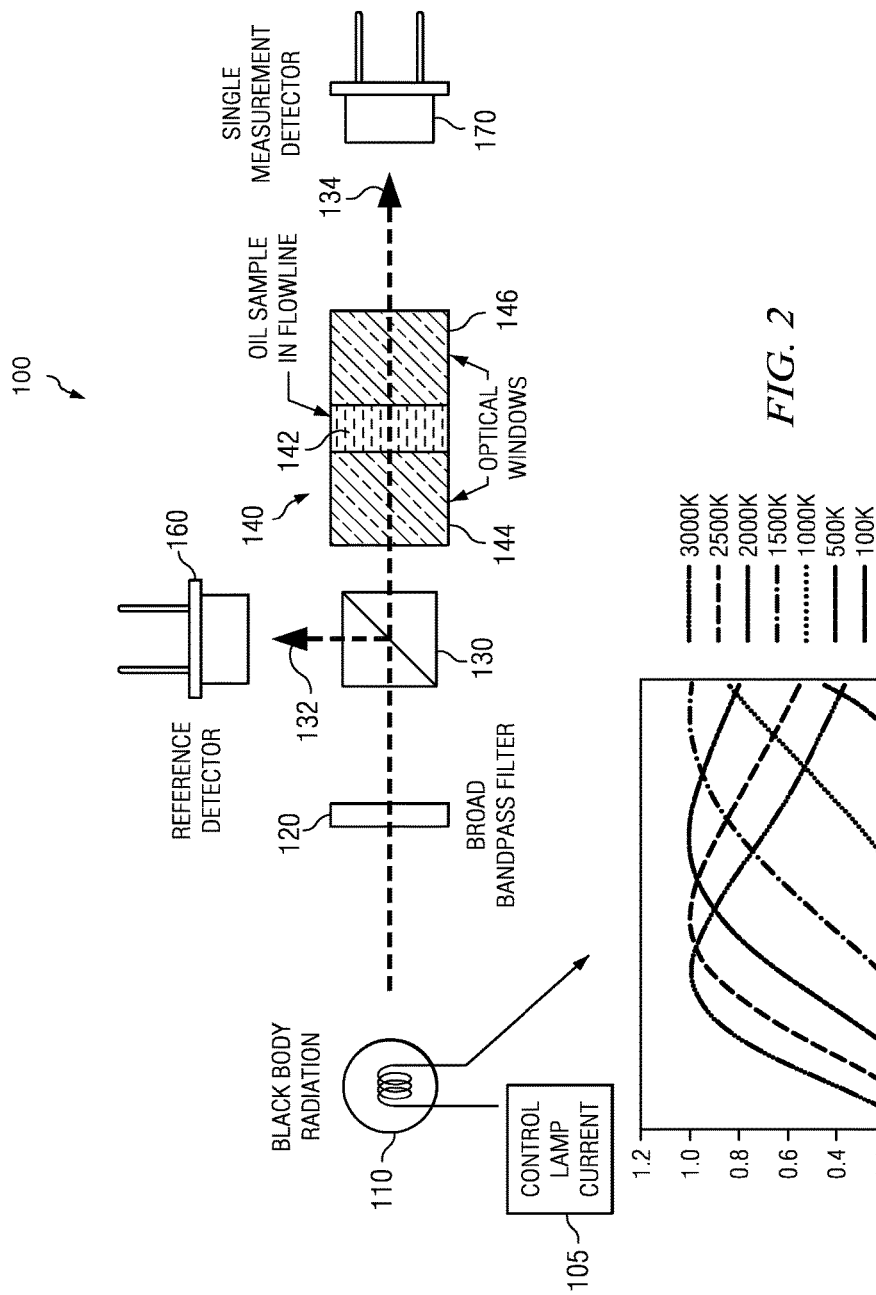
FIG. 2 depicts one example of a disclosed optical spectrometer.
Figure 3A:
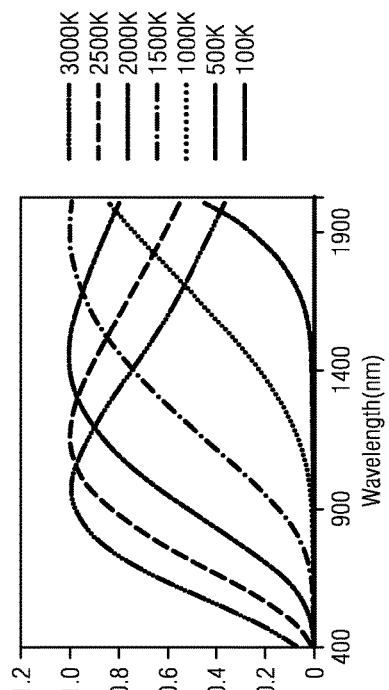
FIG. 3A depicts one example of a plot of optical intensity versus optical wavelength for a bandpass filtered near black body radiation source.

FIG. 2 depicts one example of a disclosed optical spectrometer 100. The disclosed embodiment includes a near black body type of light source 110 such as a halogen lamp. Light source 110 is connected to an electronic controller 105 which may include circuitry for controlling the electrical current or voltage provided to the light source 110 (and thereby controlling the temperature of the filament). The radiating spectral shape of the light source 110 changes predictably with temperature (or electrical current/voltage) as described in more detail below with respect to FIGS. 3A and 3B. Optical spectrometer 100 further includes a beam splitter 130 that splits incident light from the light source 110 into a first reference path 132 and a second measurement path 134. A reference detector 160 is positioned to receive light in the reference path 132. A single measurement detector 170 is positioned to receive light in the measurement path 134. A sample cell 140 including a flow line 142 through which formation fluid flows between first and second optical windows 144 and 146 (located on either side of the flow line) is positioned in the measurement path 134. Optical spectrometer 100 may further optionally include a bandpass filter 120 deployed between the light source 110 and the beam splitter 130 for selecting a desired bandwidth of the light source 110. The light source 110 may provide a broad band spectrum, for example, ranging from about 400 to about 2200 nm. The use of a bandpass filter 120 may enable a narrower band of optical energy to be utilized. The disclosed embodiments are not limited to the use of such a bandpass filter.

With continued reference to FIG. 1, the spectra generated by a halogen lamp follow Plank's law which quantifies the energy emitted by a black body (or near black body) source as a function of temperature and wavelength. As is known to those or ordinary skill in the art a black body source emits black body radiation which has a spectrum and intensity that depends only on the temperature of the emitting body (e.g., the filament).

Figure 3B:
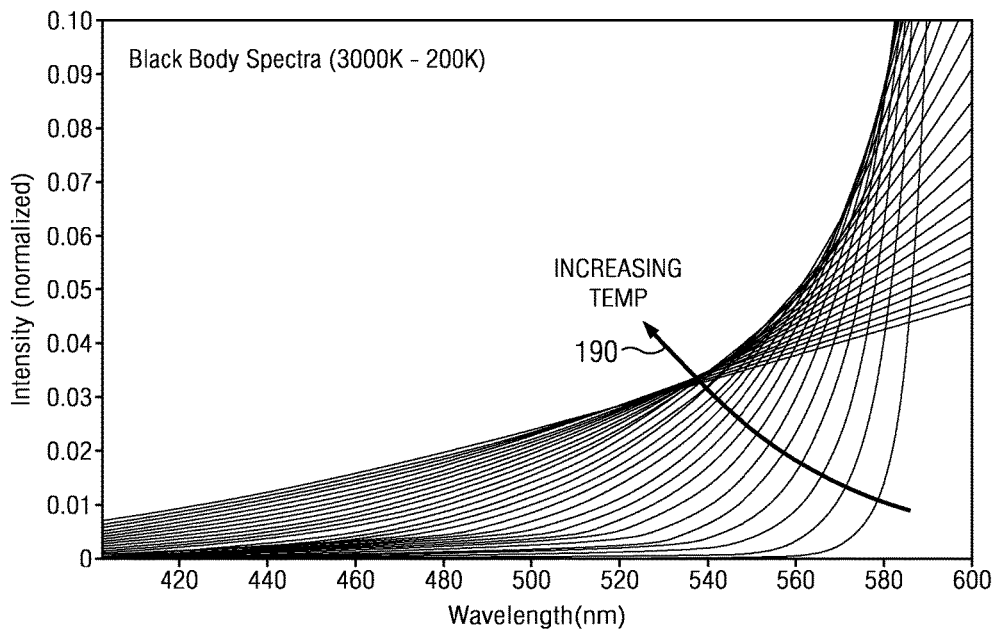
FIG. 3B depicts one example of a plot of normalized optical intensity versus optical wavelength for a bandpass filtered near black body radiation source.

The radiating spectral shape of a halogen lamp changes with filament temperature, for example, as shown on FIG. 3B, which plots normalized intensity versus wavelength (from 400 to 600 nm) at a number of filament temperatures (ranging from 200 to 3000 degrees K). As the temperature increases, the intensity of the emitted light increases at lower wavelengths (higher frequencies) as indicated at 190. As the temperature decreases the intensity of the emitted light increases at longer wavelengths (lower frequencies). The temperature of the filament (and therefore the radiating spectral shape) may be controlled via controlling the electrical current or voltage to the filament (increasing the current or voltage correspondingly increases the filament temperature).

While FIG. 3B depicts spectra in the wavelength range from 400 to 600 nm, it will be understood that the disclosed embodiments are not so limited. In various embodiments, substantially any suitable range of visible and infrared wavelengths may be utilized, for example, in a range from about 400 to about 2200 nm depending on the fluid composition to be analyzed. For example, gaseous hydrocarbon fluids may be evaluated at a wavelength range from about 1600 to about 1900 nm. Black oil and heavy oil samples may be evaluated in lower wavelength ranges, for example, from about 600 to about 1400 nm. Volatile oils may be evaluated at still lower wavelengths, for example, from about 400 to about 600 nm while water and carbon dioxide containing samples may be evaluated at higher wavelengths (e.g., greater than about 1900 nm). Again, the disclosed embodiments are not limited to the use of any particular optical wavelengths.

Figure 4:
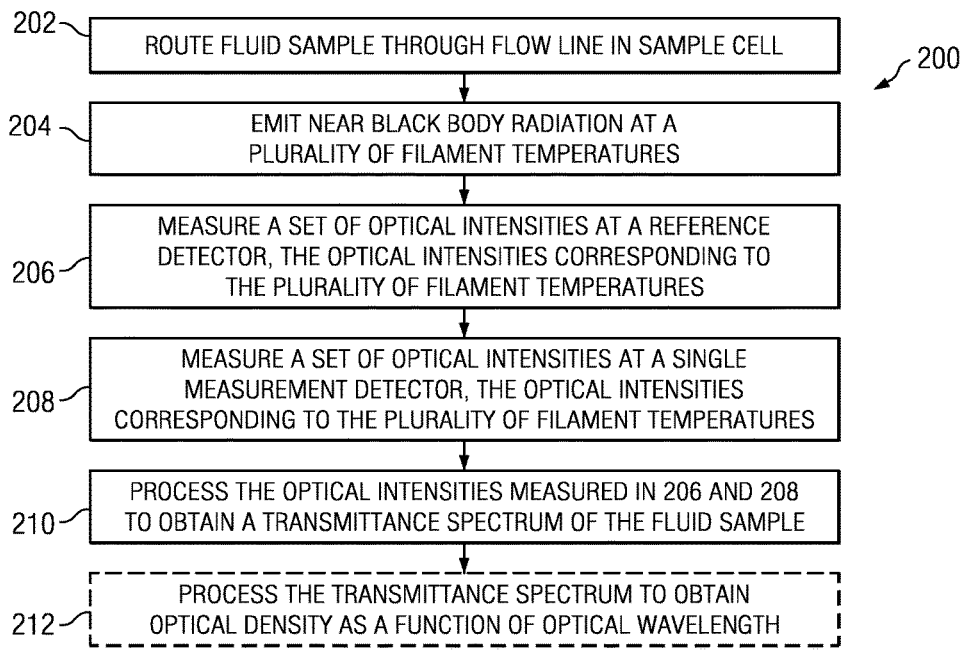
FIG. 4 depicts a flow chart of one disclosed method embodiment.

FIG. 4 depicts a flow chart of one disclosed method embodiment 200 that makes use of optical spectrometer 100. By measuring the optical transmission at various filament temperatures (or currents or voltages), a continuous optical spectrum of a reservoir fluid sample may be recovered by inverting the acquired data as described in more detail below. The disclosed method embodiments therefore may enable the measurement of optical spectra at continuous wavelengths with a single measurement detector. At 202 a fluid sample is routed though a flow line in the sample cell of an optical spectrometer (such as optical spectrometer 100 depicted on FIG. 2). Near black body radiation is emitted via a near black body radiation source at a plurality of filament temperatures (e.g. at 10 or more distinct temperatures) at 204. First and second sets of optical intensities may be measured substantially simultaneously at 206 and 28. The first set of optical intensities (corresponding to the plurality of filament temperatures) is measured at the reference detector while the second set of optical intensities (also corresponding to the plurality of filament temperatures) is measured at a measurement detector after passing through the sample cell including the fluid sample. The first and second sets of optical intensities obtained in 206 and 208 are processed at 210 to obtain a transmittance spectrum of the fluid sample. The transmittance spectrum may be optionally further processed at 212 to obtain an optical density (absorption) of the fluid sample as a function of wavelength.

The filament temperature may be incrementally stepped, for example, through a number (e.g., 10 or more) of distinct temperatures in a range from about 200 to about 3000 degrees K (e.g., at 100 degree K intervals). The filament temperature may be controlled (or set) for example via controlling the applied electrical current or voltage to the filament (e.g., via incrementally stepping the current or voltage applied to the filament through a predetermined range of values). The light source thus generates radiant spectra $h_0(\lambda), h_1(\lambda), \ldots h_n(\lambda)$ at the corresponding temperatures $T_0, T_1, \ldots, T_n$ where $h_i(\lambda)$ indicates that the spectra are functions of wavelength $\lambda$. Non limiting examples of radiant spectra are illustrated in FIG. 3B as described above. The first set of optical intensity measurements $H_0, H_1, \ldots, H_n$ are measured at the reference detector and are directly related to the corresponding radiant spectra $h_0(\lambda), h_1(\lambda), \ldots, h_n(\lambda)$. The second set of optical intensity measurements $I_0, I_1, \ldots, I_n$ are measured at the reference detector and are related to the corresponding radiant spectra $h_0(\lambda), h_1(\lambda), \ldots h_n(\lambda)$ and the transmittance (or absorbance) of the fluid sample.

The second set of optical intensity measurements may be expressed as a set of mathematical equations relating the optical intensity measurements to the radiant spectra of the light source and a transmittance spectrum of the fluid sample, for example, as follows:

$$I_0 = \int h_0(\lambda) \cdot S(\lambda) d\lambda$$
$$I_1 = \int h_1(\lambda) \cdot S(\lambda) d\lambda$$
$$I_2 = \int h_2(\lambda) \cdot S(\lambda) d\lambda$$
$$\vdots$$
$$I_n = \int h_n(\lambda) \cdot S(\lambda) d\lambda$$

Equation 1 where $S(\lambda)$ represents the unknown transmittance spectrum of the fluid sample. The set of equations given in Equation 1 may be written as a discrete inverse problem, for example, as follows:

$$HS = I$$

Equation 2 where H is a two dimensional matrix that represents the radiant spectra of the light source as a function of both filament temperature $(T_0, T_1, \ldots, T_n)$ and wavelength $(\lambda_0, \lambda_1, \ldots, \lambda_m)$, I is a one dimensional matrix that represents the second set of optical intensity measurements made at the measurement detector, and S is a one dimensional matrix that represents the transmittance spectrum of the fluid sample. H, S, and I may be represented as matrices, for example, as follows:

$$H = \begin{pmatrix} h_{T_0,\lambda_0} & h_{T_0,\lambda_1} & \cdots & h_{T_0,\lambda_m} \\ h_{T_1,\lambda_0} & h_{T_1,\lambda_1} & \cdots & h_{T_1,\lambda_m} \\ \vdots & \vdots & \ddots & \vdots \\ h_{T_n,\lambda_0} & h_{T_n,\lambda_1} & \cdots & h_{T_n,\lambda_m} \end{pmatrix}$$

Equation 3

$$S = \begin{pmatrix} S_{\lambda_0} \\ S_{\lambda_1} \\ \vdots \\ S_{\lambda_m} \end{pmatrix}$$

Equation 4

$$I = \begin{pmatrix} I_0 \\ I_1 \\ \vdots \\ I_n \end{pmatrix}$$

Equation 5

The intensity matrix I is measured at the single measurement detector at the plurality of filament temperatures (or filament voltages/currents). The two dimensional radiant spectra matrix H is computed from the first set of optical intensity measurements $H_0, H_1, \ldots, H_n$ that are measured at the reference detector based on the assumption that the light source follows Plank's law (i.e., is a black body source). For example, each of the optical intensity measurements $H_0, H_1, \ldots, H_n$ may be understood to represent the area under a corresponding one of the spectra. The individual $h_{T_i,\lambda_j}$ matrix values may be obtained by processing the shape of the spectra (e.g., in FIG. 3B) in combination with the corresponding intensity measurements at a preselected plurality of wavelengths $(\lambda_0, \lambda_1, \ldots, \lambda_m)$.

Since H and I are thus known, the transmittance spectrum S can be estimated, for example, as follows:

$$S = (H^T H)^{-1} H^T I$$

Equation 6 where the superscript T represents the matrix transpose operation such that $H^T$ represents the transpose of the two dimensional radiant spectra matrix H. The transmittance spectrum S may be further processed to obtain an optical density (absorbance) as a function of wavelength, for example, as follows:

$$OD(\lambda_i) = -\log S(\lambda_i)$$

Equation 7 where $OD(\lambda_i)$ represents the wavelength dependent optical density of the fluid sample.

The disclosed embodiments are now described in further detail by way of the following non-limiting example. A hypothetical optical spectrometer was used to estimate absorbance values of first and second phenol red samples at various wavelengths. The first phenol red sample had a pH of 4 while the second phenol red sample had a pH of 7. The computed absorbance values were compared with control spectra that were obtained via a conventional laboratory spectrometer. The hypothetical spectrometer was similar to the embodiment depicted on FIG. 2 and included a bandpass filter having a pass band in the range from about 400 nm to about 650 nm and a 50:50 beam splitter arrangement.

Figure 5:
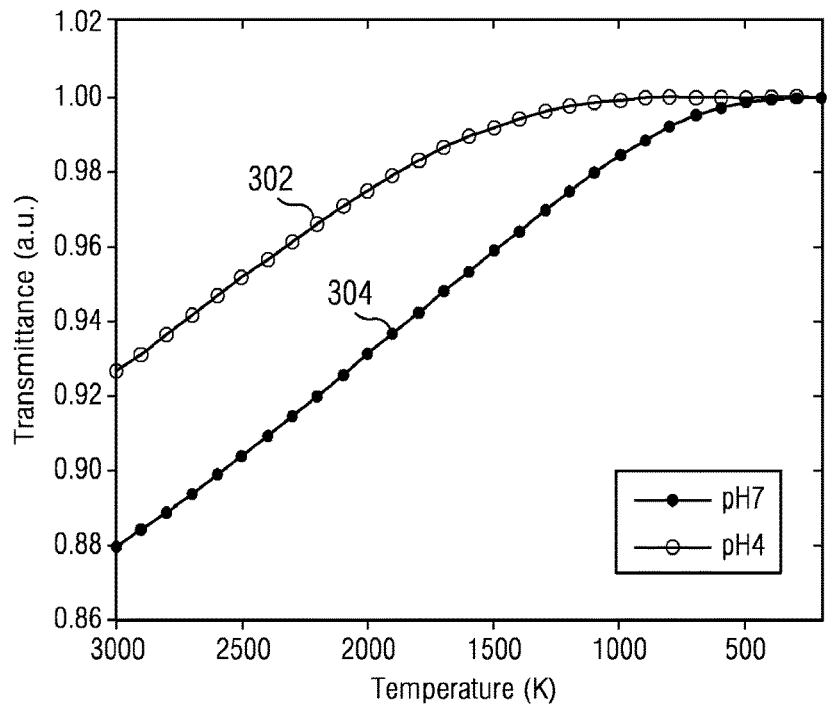
FIG. 5 depicts one example of a plot of optical transmittance versus temperature.

FIG. 5 depicts a plot of optical transmittance versus temperature (degrees K) at 100 degree K intervals (for a total of 29 measurements in the range from 200 to 3000 degrees K). The data for the pH 4 phenol red sample is shown at 302 while the pH 7 phenol red sample is shown at 304. The data depicted on FIG. 5 may be thought of as normalized raw intensity data obtained at the measurement detector at each temperature. Likewise, when a 50:50 beam splitter is utilized, the data depicted on FIG. 5 may also be thought of as ratios of the raw intensity data obtained at the measurement detector to the raw intensity data obtained at the reference detector at each temperature. The I matrices (for each of the pH 4 and pH 7 samples) were defined to include the 29 measurement values depicted on FIG. 5. The H matrices (for each of the pH 4 and pH 7 samples) were computed at 25 nm intervals in wavelength from the known temperatures and the shape of the spectra depicted on FIG. 3A.

Figure 6:
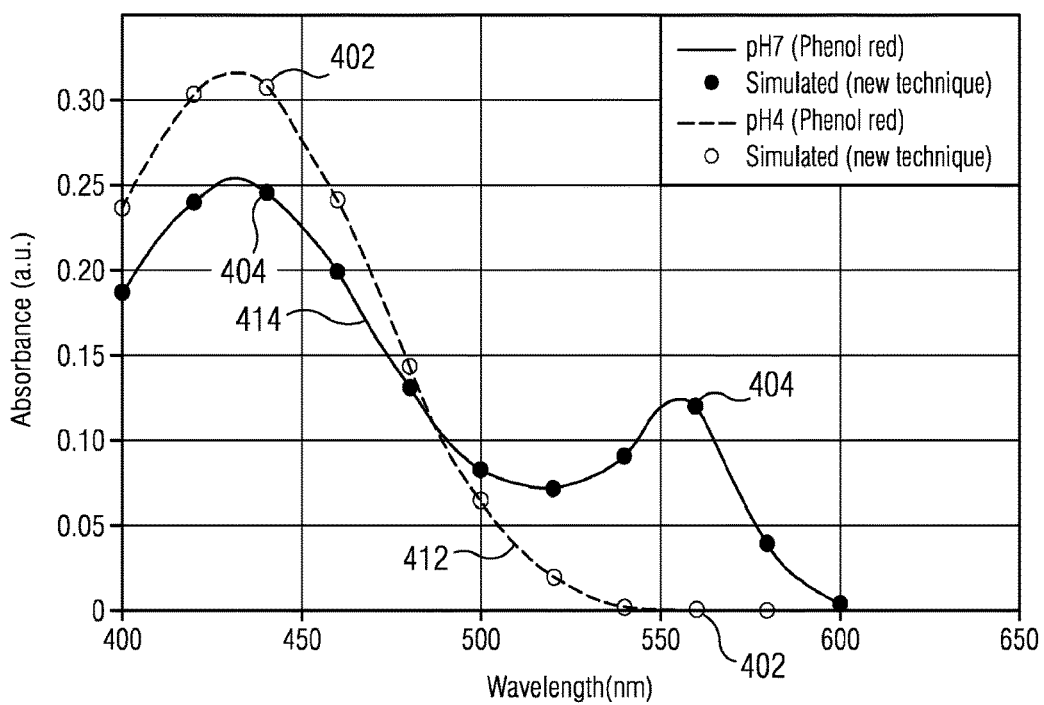
FIG. 6 depicts one example of a plot of absorbance versus optical wavelength.

FIG. 6 depicts a plot of absorbance (optical density) versus wavelength for the pH 4 and pH 7 phenol red samples. Upon obtaining the I and H matrices, transmittance spectra S were computed for each sample as described above with respect to Equation 6. The absorbance (optical density) was computed from the transmittance spectra as described above with respect to Equation 7. FIG. 6 depicts computed absorbance values at 25 nm intervals for the pH 4 phenol red sample at 402 and the pH 7 phenol red sample at 404. Corresponding laboratory spectrometer absorbance spectra are depicted at 412 and 414 for the pH 4 and pH 7 phenol red samples. Note the high degree of agreement between the absorbance values computed using the disclosed methodology and the control spectra obtained using the laboratory spectrometer.

Although an optical spectrometer and methods for making optical spectrometry measurements and certain advantages thereof have been described in detail, it should be understood that various changes, substitutions and alternations can be made herein without departing from the spirit and scope of the disclosure as defined by the appended claims.

What is claimed is:

1. A method for obtaining a substantially continuous transmittance spectrum of a fluid sample, the method comprising:
    (a) receiving the fluid sample at an optical spectrometer;
    (b) emitting near black body optical energy at a plurality of filament temperatures by incrementing an applied electrical current or electrical voltage through a predetermined range of values, the optical energy passing through a beam splitter into first and second optical paths, the second optical path passing through the fluid sample;
    (c) measuring a first set of optical intensities at a reference detector in the first path, the optical intensities in the first set corresponding to the plurality of filament temperatures;
    (d) measuring a second set of optical intensities at a single measurement detector in the second optical path, the optical intensities in the second set corresponding to the plurality of filament temperatures, and wherein no filter is disposed between the beam splitter and the single measurement detector; and
    (e) processing the optical intensities measured in (c) and (d) to compute the substantially continuous transmittance spectrum of the fluid sample;
    wherein computing the transmittance spectrum comprises solving the integral equation:
    $$I_n = \int h_n(\lambda) \cdot S(\lambda) d\lambda$$
    wherein I represents optical density, h represents radiant spectrum, $\lambda$ represents wavelength, S represents transmittance spectrum, and n represents an integer.

2. The method of claim 1, further comprising:
    (f) processing the transmittance spectrum obtained in (e) to compute an optical density of the fluid sample.

3. The method of claim 1, wherein (e) further comprises:
    (i) processing the first set of optical intensities measured in (c) in combination with shapes of corresponding spectra of the optical energy emitted in (b) to compute a two dimensional matrix of radiant spectra values; and
    (ii) processing the two dimensional matrix of radiant spectra values in combination with the second set of optical intensities measured in (d) to compute the transmittance spectrum of the fluid sample.

4. The method of claim 3, wherein the transmittance spectrum of the fluid sample is computed according to the following mathematical equation:
$$S = (H^T H)^{-1} H^T I$$
    wherein S represents the transmittance spectrum in one dimensional matrix form, H represents the two dimensional matrix of radiant spectra values, $H^T$ represents a transpose of the two dimensional matrix H, and I represents the second set of optical intensity measurements in one dimensional matrix form.

* * * * *